(12) United States Patent
Koch (10) Patent No.: US 6,351,665 B1
(45) Date of Patent: Feb. 26, 2002

(54) METHOD AND APPARATUS FOR EVALUATING MYOELECTRIC SIGNALS AND IDENTIFYING ARTIFACT

(76) Inventor: Kenneth L Koch, 353 Maple Ave., Hershey, PA (US) 17033

(*) Notice: Subject to any disclaimer, the term of this patent is extended or adjusted under 35 U.S.C. 154(b) by 0 days.

(21) Appl. No.: 09/547,140

(22) Filed: Apr. 11, 2000

Related U.S. Application Data (60) Provisional application No. 60/133,128, filed on May 7, 1999, and provisional application No. 60/147,172, filed on Aug. 5, 1999.

(51) Int. Cl.[7] .................................................. A61B 5/04
(52) U.S. Cl. ...................................... 600/546; 600/595
(58) Field of Search ............................... 600/546, 547, 600/593

(56) References Cited

U.S. PATENT DOCUMENTS

| | | |
|---|---|---|
| 5,109,870 A | 5/1992 | Silny et al. |
| 5,161,539 A | 11/1992 | Evans et al. |
| 5,197,479 A | 3/1993 | Hubelbank et al. |
| 5,292,344 A | 3/1994 | Douglas |
| 5,365,428 A | 11/1994 | dePinto et al. |
| 5,545,638 A | 8/1996 | Greenwood |
| 5,619,995 A | 4/1997 | Lobodzinski |
| 5,626,876 A | 5/1997 | Müller |
| 5,657,759 A | 8/1997 | Essen-Moller |
| 5,667,794 A | 9/1997 | Simon et al. |
| 5,681,827 A | 10/1997 | Field |
| 5,690,691 A | 11/1997 | Chen et al. |
| 5,701,894 A | 12/1997 | Cherry et al. |
| 5,704,368 A | 1/1998 | Asano et al. |
| 5,770,181 A | 6/1998 | Kirkland |
| 5,776,073 A * | 7/1998 | Garfield et al. .............. 600/546 |
| 5,795,304 A | 8/1998 | Sun et al. |
| 5,797,840 A | 8/1998 | Akselrod et al. |
| 5,820,556 A | 10/1998 | Essen-Moller |
| 5,836,994 A | 11/1998 | Bourgeois |
| 5,840,332 A | 11/1998 | Lerner et al. |
| 5,845,808 A | 12/1998 | Kani |
| 5,857,980 A | 1/1999 | Wilson |
| 5,861,014 A | 1/1999 | Familoni |
| 5,879,325 A | 3/1999 | Lindström et al. |

OTHER PUBLICATIONS

Koch et al., "Gastric Electrical Activity, Gastric Emptying and the Water Load Test in Evaluating Patients with Functional Dyspepsia Symptoms", American College of Gastro. Mtg.—Abstract (Jun. 4, 1998).

Koch et al., "Provocative Water Loading and Gastric Myoelectrical Activity in patients with Dysmotility–Like Dyspepsia", Symposium on Gastrointestinal Motility—Abstract (Feb. 15–20, 1998).

Koch et al., "Abnormal and Normal Electrogastrograms (EGG) in Patients with Functional Dyspepsia".

(List continued on next page.)

Primary Examiner—John P. Lacyk
Assistant Examiner—Pamela L Wingood
(74) Attorney, Agent, or Firm—Manelli, Denison & Selter; Edward J. Stemberger

(57) ABSTRACT

An apparatus and method of identifying artifacts in signals indicative of detected myoelectrical activity is provided. The method includes providing electrodes to obtain a plurality of first signals over time. The first signals are produced from an internal organ in the abdominal cavity of a living being. The first signals include spurious signals as a result of artifact. A sensor obtains a plurality of second signals simultaneously as the first signals are obtained. The second signals are indicative of a respiratory function of the living being and include spurious signals indicative of artifact. The first and second signals are recorded simultaneously. The occurrence of artifacts is identified by noting irregularities in both the recorded first and second signals during a particular time frame.

31 Claims, 9 Drawing Sheets

OTHER PUBLICATIONS

Koch et al., "Effect of Physiological Gastric Distention on Nausea, Stomach Fullness, Satiety and Gastric Myoelectrical Activity in Patients with Irritable Bowel Syndrome", American Gastroenterological Association and American Association for the Study of Live Disease—Abstract (May 11–14, 1997).

Koch et al., "Gastric Emptying and Gastric Myoelectrical Activity in Patient with Diabetic Gastropareses: Effect of Ling–Term Domperidone Treatment", *The Am. Journal of Gastroenterology*, 84:9, pp. 1069–1075 (Sep., 1989).

Stern et al., "Electrogastrography: Current Issue in Validation and Methodology", *Psychophysiology*, 24:1, pp. 55–64 (Jan., 1987).

Koch et al., "Gastric Myoelectrical Activity in Premature and Term Infants", *J. Gastrointest. Mot.*, 5:1, pp. 41–47 (Mar., 1993).

Koch et al., "Electrogastrographic Data Aquisition and Analysis", *Electrogastrography: Principles and Applications*, pp. 31–44 (1994).

Koch et al., "Nausea and Vomiting and Gastric Dysrhythmias", *Electrogastrography: Principles and Applications*, pp. 309–330 (1994).

Koch, "Clinical Approaches to Unexplained Nausea and Vomiting", *Advances in Gastroenterology, Hepatology & Clinical Nutrition*, 3:4, pp. 163–178 (1998).

Koch, "Dyspepsia of Unknown Origin: Pathophysiology, Diagnosis, and Treatment", *Dig. Dis.*, 15, pp. 316–329 (1997).

Parkman et al., "Gastroduodenal Motility and Dysmotility: An Update on Techniques Available for Evaluation", *The Am. Jnl. Of Gastroenterology*, 90:6, pp. 869–892 (Jun., 1995).

\* cited by examiner

| MINUTES | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | x | x | x | | x | | | | | | | | x | x | x | | | | | | | | | x | | | | | | | | | | | | x = ARTIFACT; DATA EXCLUDED

METHOD AND APPARATUS FOR EVALUATING MYOELECTRIC SIGNALS AND IDENTIFYING ARTIFACT

This application is based on and claims priority from U.S. Provisional Application No. 60/133,128, filed May 7, 1999 and U.S. Provisional Application No. 60/147,172, filed Aug. 5, 1999.

BACKGROUND OF THE INVENTION

This invention relates generally to methods and apparatus for monitoring myoelectric signals from an organ to aid in the diagnosis of various disorders. The general term for the system of the invention is an electroviscerogram (EVG) system which measures myoelectrical activity from various organs within the abdominal cavity. Specifically, this invention relates to the use of an electrogastrogram (EGG) and analysis of electrogastrograms to diagnose recorded signals associated with functional dyspepsia and other functional or neuromuscular disorders of the gastrointestinal and urinary tract.

Nausea is a vague and sometimes difficult to describe "sick to the stomach" sensation that may evolve into an urge to vomit if the nausea becomes severe. Nausea often is a debilitating and depressing symptom. Nausea and vomiting may present as acute and self-limited symptoms that accompany a variety of diseases and disorders. For the family physician, internist, or gastroenterologist who is evaluating the patient with nausea and vomiting, there are many possible causes to consider. The gastroenterologist may be asked to see such patients in consultation, particularly if the nausea and vomiting becomes chronic. These patients may be difficult to manage if standard tests such as ultrasound of the gallbladder and pancreas, upper endoscopy, and abdominal CAT scans are normal or empiric treatment does not relieve the symptoms.

Electrogastrograms have been employed to diagnose stomach disorders. However, spurious signals (artifact) are typically present in the raw EGG signals due to patient movement, breathing, etc. These spurious signals should be excluded from any calculations used to analyze the EGG signal. Typically, spurious signals such as electrocardiogram (EKG) signals are excluded by filtering the EGG signal. However, in certain instances, the spurious signals are respiratory signals that occur in the frequency ranges of interest.

Accordingly, there is a need to provide a method and apparatus to evaluate myoelectric signals from the stomach or other intra-abdominal organs to aid in a diagnosis of a disorder and to accurately identify and exclude spurious signals.

SUMMARY OF THE INVENTION

An object of the present invention is to fulfill the need referred to above. In accordance with the principles of the present invention, this objective is obtained by providing a system for processing signals indicative of the detected myoelectrical activity. The system includes electrodes to obtain first signals over time. The first signals are produced from an internal organ in the abdominal cavity of a living being and may include spurious signals as a result of artifact. A sensor obtains second signals simultaneously as the first signals are obtained. The second signals are indicative of a respiratory function of the living being and include spurious signals indicative of artifact such as movement of the body or limbs. A processor analyzes the first signals which occur at times when artifact is not present in both of the first and second signals.

In accordance with another aspect of the invention, a method of identifying artifacts in signals indicative of detected myoelectrical activity includes:
providing electrodes to obtain first signals over time, the first signals being produced from an internal organ in the abdominal cavity of a living being, the first signals including spurious signals as a result of artifact,
providing a sensor to obtain second signals simultaneously as the first signals are obtained, the second signals being indicative of a respiratory function of the living being and include spurious signals indicative of artifact,
recording the first and second signals simultaneously,
identifying when artifacts occur by noting irregularities in both the recorded first and second signals during a particular time frame.

In another aspect of the invention, a method of monitoring the myoelectrical activity of the stomach of a person includes:
mounting electrodes on an abdomen of the person to obtain a plurality of first analog signals from the stomach over time, the first analog signals including spurious signals as a result of artifact,
mounting a sensor to the person to obtain a plurality of second analog signals simultaneously as the first analog signals are obtained, the second analog signals being indicative of a respiratory function of the person and include spurious signals indicative of artifact,
consuming, by the person, water in a specific time frame until the stomach is substantially full to stimulate gastric electro-contractile activity while recording the first and second analog signals simultaneously,
continuing to record the first and second analog signals simultaneously for a period of time after consumption of water,
identifying, during the recording of the first and second signals, the occurrence of artifacts by noting irregularities in both the first and second analog signals during a particular time frame,
converting the first analog signals to digital signals, and
analyzing the digital signals which occur at times when artifact is not present.

In yet another aspect of the invention a kit is provided for use in recording myoelectric activity of the stomach of a person. The kit includes a plurality of disposable electrodes; a visual analog scale for scoring an intensity of selected symptoms at various times; and two, one liter bottles of spring water with each bottle being scored with ml marks for accurate measurement of the volume of water consumed from the bottle.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

Figure 1:
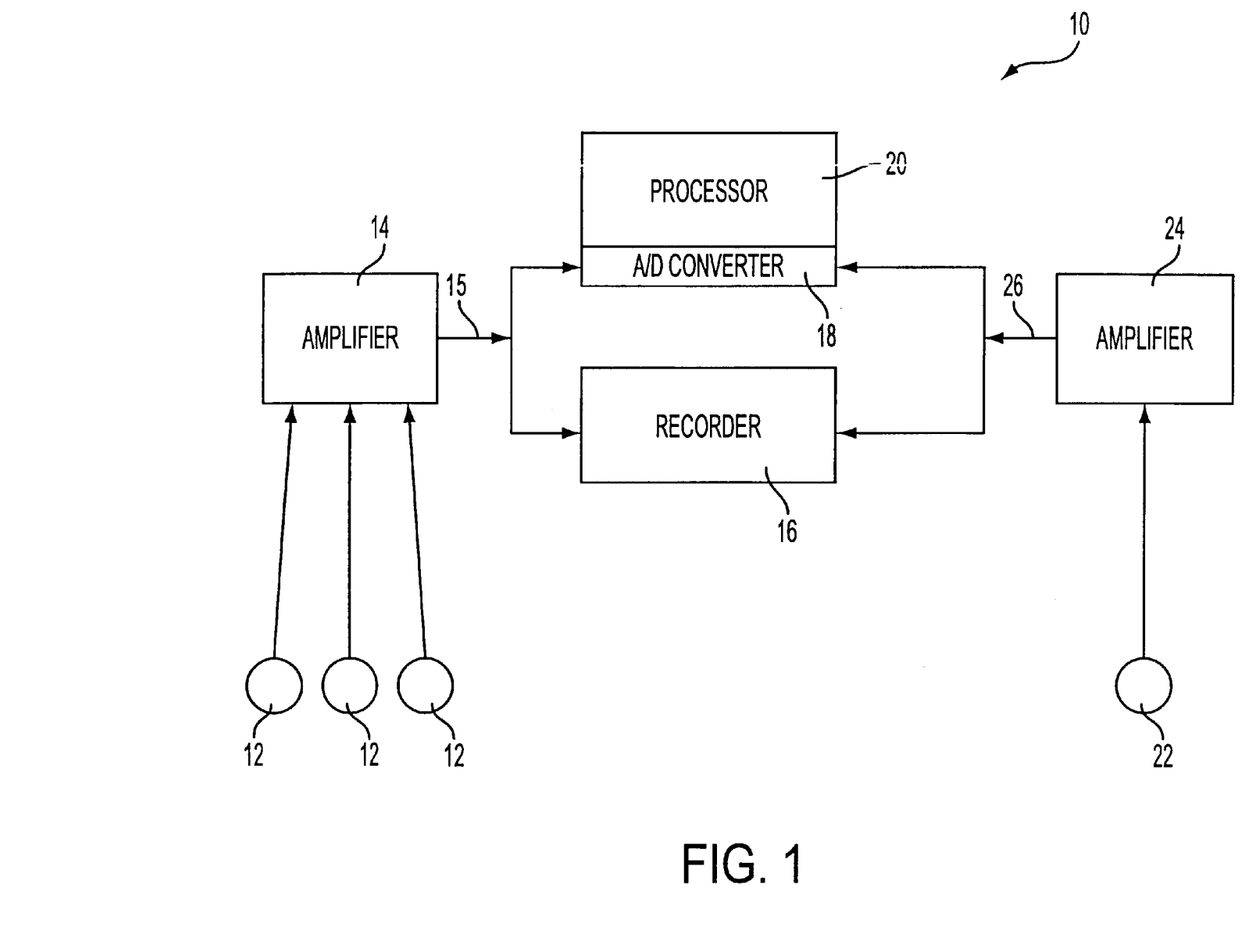
FIG. 1 is a schematic illustration of an EGG system, provided in accordance with the principles of the present invention.

With reference to FIG. 1, a system, provided in accordance with the principles of the present invention is shown, generally indicated at 10, for monitoring myoelectric signals from an organ to aid in the diagnosis of various disorders. The general term for the system 10 of the invention is an electroviscerogram (EVG) system which measures myoelectrical activity from various organs within the abdominal cavity. The device uses EKG-type electrodes placed over the relevant regions of the abdomen for recording the electrical activity from the selected organ(s) of interest.

The EVG system includes a family of devices designed to provide the following recordings:

1) Electrogastrogram (EGG)—myoelectrical activity from the stomach,
2) Electroduodenogram (EDG)—myoelectrical activity from the duodenum,
3) Electrointestinogram (EIG)—myoelectrical activity from the small intestine,
4) Electrosigmoidocologram (ESCG)—myoelectrical activity from the sigmoid colon and other areas of the colon,
5) Electrovesiculogram (EVEG)—myoelectrical activity from the urinary bladder, and
6) Electrofallopiogram (EFG)—myoelectrical activity from the oviduct.

In the illustrated embodiment, the system 10 is configured as an electrogastrogram (EGG). In particular, the EGG signal is a bioelectrical signal recorded from the skin surface that reflects the myoelectrical activity of the stomach.

Figure 2:
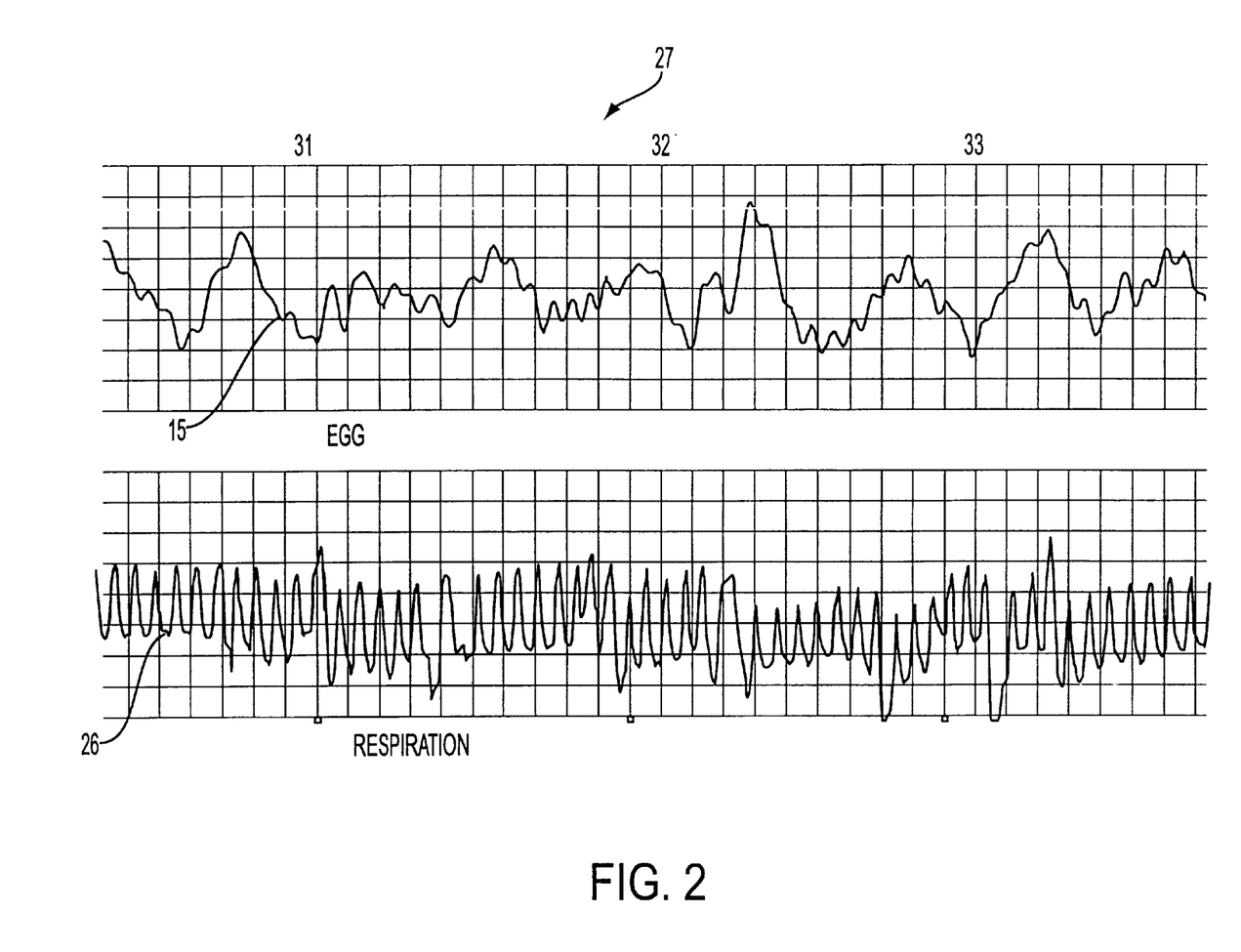
FIG. 2 is a view of data from a strip chart recorder obtained with the system of FIG. 1, showing an upper channel which records an EGG signal and a lower channel which simultaneously records a respiratory signal.
Figure 3:
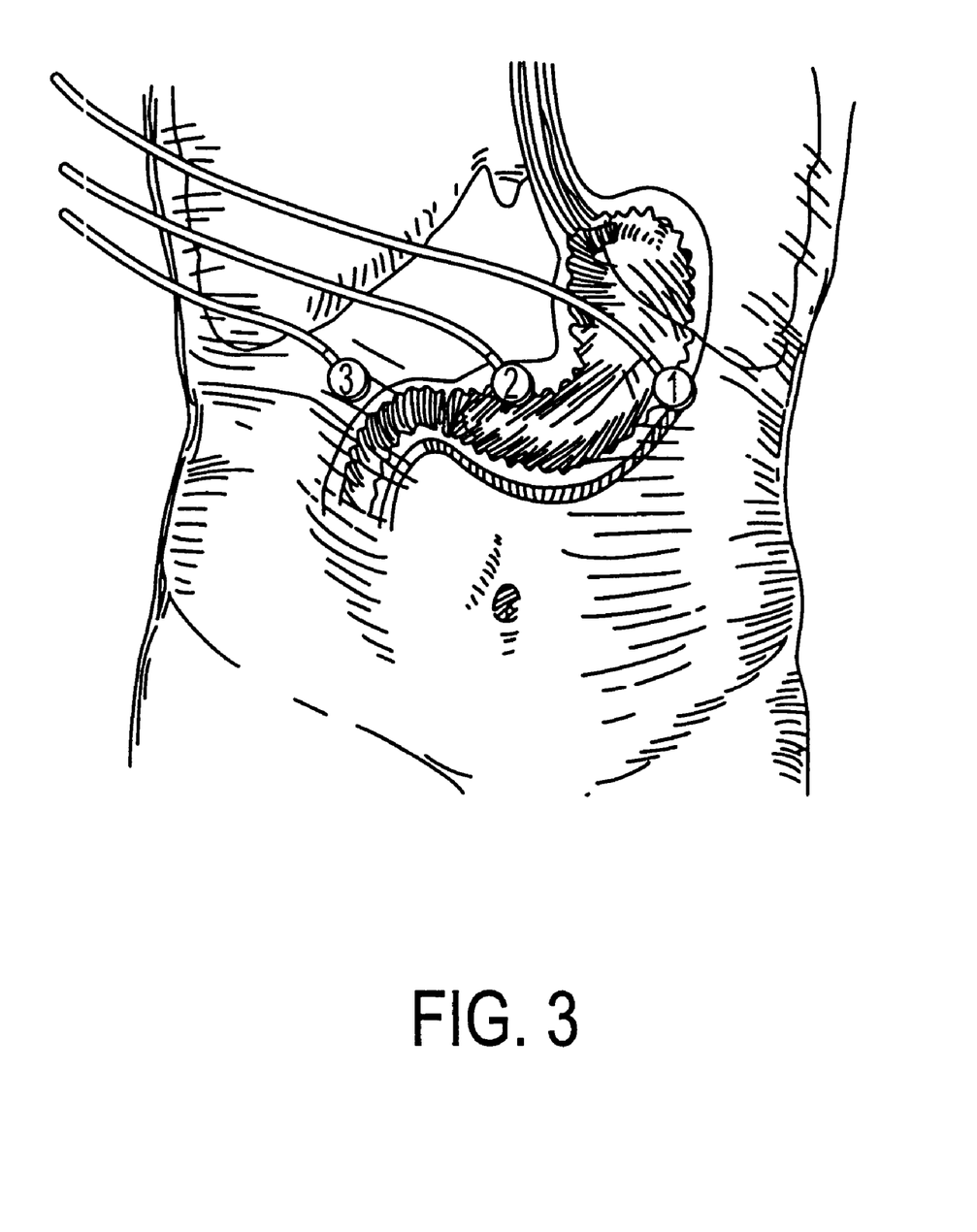
FIG. 3 is an illustration of a human abdomen and the placement of electrodes thereon, in accordance with the invention.

The system 10 comprises at least three standard silver-silver chloride electrodes 12 connected through an isolation cable to an amplifier 14. As shown in FIG. 3, electrode #1 is positioned in the mid-clavicular line (left side) approximately two inches below the left costochondral margin. Electrode #2 is located on the mid-point between the xiphoid and umbilicus. Electrode #3 is placed on a line formed by electrodes 1 and 2 and a line from the mid-clavicular line (right side) to a point generally two inches below the right costochondral margin. Electrode #3 is the reference or "ground" electrode. The electrodes 12 reflect the raw, analog EGG signal. The amplifier 14 is a Bioamplifier and is used to amplify the analog EGG signal. The amplified EGG signal 15 is sent to an upper channel (FIG. 2) of a strip chart recorder 16 for a hard a copy thereof. In addition, the amplified EGG signal 15 is sent to an A/D converter 18 of a computer 20 for digitization of the analog EGG signal for software analysis. In the Illustrated embodiment, the A/D converter 18 is a card of computer 20. It can be appreciated that the AND converter 18 may be a device separate from the computer 20.

The amplifier 14 is a conventional physiological amplifier, whose filter characteristics have been adjusted to allow any biological signal with an approximate frequency range of from 1 to 15 cycles per minute (cpm) to pass through the established window for recording and digitization. These filter ranges encompass the physiologically relevant ranges with which to record electrogastrogram (EGG) signals.

In accordance with the invention, a respiration belt 22 is provided and is fitted snugly to the upper chest (under the arm pits) of the patient. An amplifier 24, preferably a conventional pressure transducer amplifier, is used to amplify an analog respiration signal from the respiration belt 22. The amplified respiration signal 26 is sent to the lower channel of the strip chart recorder (FIG. 2). The strip chart paper 27 is printed with marks placed in one minute intervals. Each minute must be manually numbered on the strip chart paper once the recording of the respiration signal 26 and EGG signal 15 commences, the function of which will be explained below. In addition, the amplified analog respiration signal 26 is sent to the A/D converter 18 of the computer 20 and converter to a digital signal. The respiration signal 26 is used for recording respiration activity and also alterations in the respiration reflect artifacts (spurious signal conditions) in the concurrently recorded EGG signal 15. More particularly, the inspection of the respiration signal 26 allows the operator to detect the following important artifacts in the EGG signals:

1) Artifacts in the EGG signal caused by movement of the patient's limbs, or torso,
2) Artifacts in the EGG signal caused by respiration movements such as deep breaths, sighs, coughs, and talking,
3) Respiration artifacts e EGG signal that are rhythmic signals less that 10 cycles per minute (cpm) that are consistent with tachygastria but are actually slow respiratory signals, and
4) Respiration artifacts in the EGG signal that are rhythmic signals greater that 10 cpm that are consistent with duodenal frequencies but are actually respiratory signals.

The detection of artifacts will be explained more fully below.

Preparation of the patient for reliable and reproducible EGG recording preferably includes the consumption by the patient of eight ounces of apple juice and two pieces of dry toast two hours prior to the start of the EGG recording process. The patient should then fast for two hours immediately preceding the session. If consistent with the patients well being, drugs which produce myoelectrical or contractile activity (e.g., narcotics, prokinetid agents) should be discontinued for 48 hours prior to the recording.

The following practical points will help insure a quality EGG recording:

1) Record the EGG in a quiet room with subdued light,
2) Avoid loud noises or distracting voices,
3) Position the patient in a comfortable chair or recliner,
4) Instruct the patient to keep arms and legs still and to avoid, in particular, quick body movements,
5) The patient should avoid talking during the recording.

Once the patient is prepared for recording, recording of the EGG signal can commence. The strip chart will simultaneously record the EGG signal 15 and the respiration signal 26. As noted above, there are marks on the strip chart paper to designate each minute of elapsed time. At the computer 20, the operator can run software to digitize the EGG signal 15 and the respiration signal 26. The program should be run to coincide as closely as possible with the recording of a new minute of data on the strip chart, as indicated by the marks on the top of the chart paper 27. This begins the digitization of the EGG signal 15. The operator should mark a "0" to the initial minute on the strip chart paper 27 and continue to record the elapsed minutes directly on the chart paper 27 from this point on to the conclusion of the recording session. Two to four channels are digitized routinely.

Throughout the recording, the operator must continuously observe the patient and note on the strip chart paper 27 any events such as limb movement, speaking, or coughing, which might produce artifact in the EGG signal. Any artifacts are usually obvious as sudden changes in the EGG wave (signal) contours with deflections that may go off-scale or acutely deform the EGG signal 15. Artifact is often, but not always, accompanied by a simultaneous disturbance in the respiration channel. The notations made on the strip chart paper during the recording session will facilitate later review and exclusion of artifact from the data analysis. This baseline or preprandial portion of the recording should be continued to obtain about 15 minutes of useable data.

Once the baseline data has been recorded, a water load test is administered as described below. The EGG recording is not discontinued during the patient's ingestion of water.

The water load test provided in accordance with the invention provides a provocative event that stimulates gastric electro-contractile activity. The patient is given one 32 ounce container of water and is to drink the water in a five minute time frame until his or her stomach feels "full". The patient need not consume the entire 32 ounces of water. However, for some patients to feel "full" at least a portion of another 32 ounce container of water will be needed. The water load test provides a non-caloric physical volume for the stomach and the subsequent myoelectrical activity. The operator marks the start and finish time of the drinking until full period on the chart paper and records the amount of water consumed in ounces and ml on the chart paper. Several symptoms (nausea, satiety, stomach fullness, and bloating) are rated before and after the water load test. The intensity of these symptoms is rated on a visual analog scale.

Figure 4:
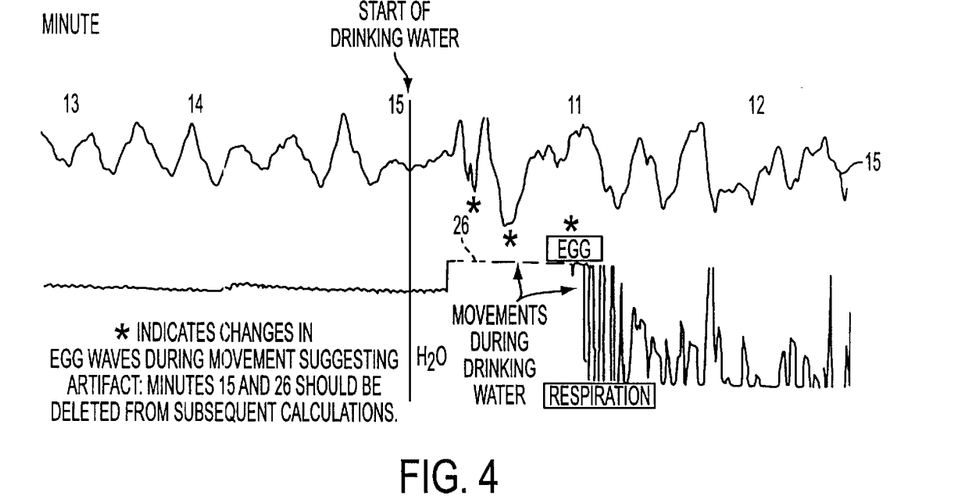
FIG. 4 shows artifact in the EGG signal and corresponding changes in respiratory rate during the ingestion of water by the patient.
Figure 5:
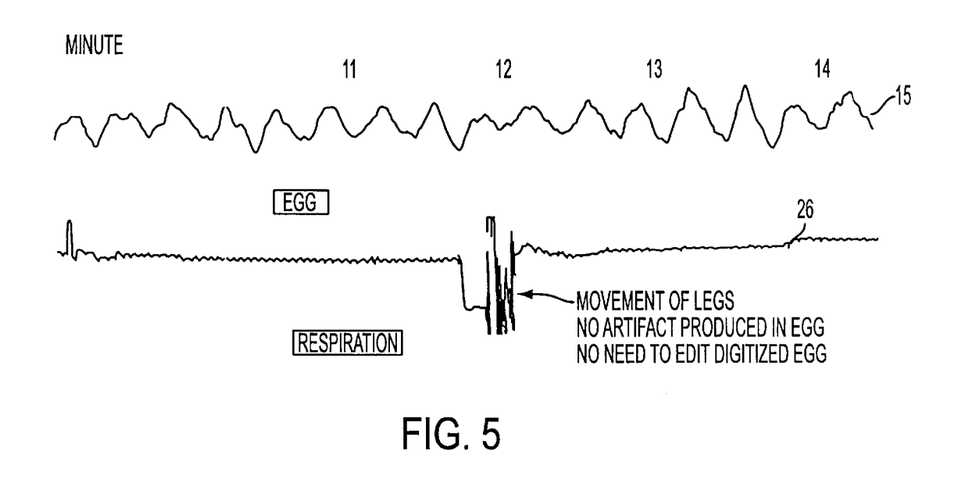
FIG. 5 shows limb movement recorded by the respiratory channel with no significant change in the EGG signal.

An example of the strip chart during a water load test is shown in FIG. 4. As can be seen, the disruption in the respiration signal 26 channel is matched by a qualitative change in the EGG signal 15, both in amplitude and in frequency. In this example, minutes 15 and 16 should be excluded from subsequent calculations. The EGG recording is continued for 30 additional minutes after the ingestion of the water load has been completed. The operator continues observing the patient for events which might produce artifact and notes their occurrence on the chart paper. FIG. 5 shows a strip chart indicating on the respiration channel 26 that the patient moved his legs, without disrupting the EGG signal 15. Thus, no artifact resulted. Minutes where an artifact occurs in both the EGG signal 15 and the respiration signal 26 should be excluded from further calculations. However, if an irregularity in the EGG signal 15 occurs and the corresponding respiration signal 26 remains regular, then the minutes when the EGG signal is irregular can be included in further calculations.

After the 30 minute period, the EGG recording is complete. The digitized EGG file, which has been stored on the computer's internal hard drive is now analyzed using proprietary software to obtain the following reports: A summary data sheet is generated containing the power, percentage distribution of power and ratios in the four frequency ranges of interest:

1.0–2.5 cpm (bradygastria)
2.5–3.75 cpm (normal)
3.75–10.0 cpm (tachygastria)
10.0–15.0 cpm (duodenal) (Note: slow respiratory rhythms may occur in this frequency range.

First, the raw EGG rhythm strip (from the strip chart) is inspected to identify artifact in the EGG signal by viewing both the EGG signal 15 and the corresponding respiration signal 26 to select the appropriate minutes from the EGG rhythm strip for computer analysis. For purposes of illustration, the following analysis involves hypothetical subject "John Doe" (JD).

Baseline (Preprandial) Period

The raw EGG strip is reviewed minute by minute for obvious movement artifact in the EGG signal. As noted above, these artifacts include times when the EGG signal 15 and the respiration signal 24 go off scale at the top or bottom of the channel or when abrupt extremely narrow changes occur in the wave configurations thereof. Notations by the operator indicating movement or other activities that might affect the EGG signal are also reviewed. EGG frequencies in the 3.75–10.0 cpm range are compared with respiratory frequencies to confirm that these EGG frequencies in the tachygastria range are not respiratory frequencies. A similar comparison of EGG and respiratory frequencies is performed for frequencies in the EGG signal from 10–15 cpm. The program will permit minutes containing artifact to be disregarded for purposes of data analysis.

In patient JD, minutes 0 to 10 are chosen from the baseline recording. Thus, the artifact free baseline recording was for 10 minutes. A baseline recording duration from 10–15 minutes is optimal. (At least five consecutive minutes of artifact-free EGG signal are needed for computer analysis.)

Water Ingestion Period

The water ingestion interval of the EGG signal is reviewed next. Patient JD took four minutes to drink water until full. A total of 1000 cc was ingested during minutes 11, 12, 13 and 14. Artifact almost always occur during this period of EGG recording and these minutes will be excluded from analysis.

Period After Water Ingestion (Postprandial Period)

After water ingestion is completed, three consecutive ten minute periods of EGG signal will be analyzed. Artifact can occur at any time during these in minute periods, so the actual minutes selected for computer analysis may be less than 10 for each period. The EGG rhythm strip is now examined in these postprandial time periods. The first postprandial ten minute period includes minutes 15 to 24. In the illustrative example, the EGG signal appeared stable and without artifact except for minute 24 where movement artifact was noted. Thus, minutes 15 through 23 are chosen for computer analysis; minute 24 is excluded.

The second ten minute period (i.e., minutes 10 through 20 after water ingestion) encompasses minutes 25 through 34. Minutes 25 and 26 contain artifact and are therefore not selected. The minutes selected for computer analysis are minutes 27 through 33; minute 34 is excluded since it contains artifact due to coughing, as reflected on the strip chart paper.

Finally, the third ten minute period (i.e., minutes 20 through 30 after water ingestion) encompasses minutes 35 through 44. Note that the computer analysis program normally deletes the final 1 or 2 minutes for computational reasons. Thus, a total of 42 or 43 minutes may actually be available for computer analysis. No artifact was present in these minutes of EGG signal. Accordingly, minutes 35 through 43 will be selected for computer analysis.

Figure 6:
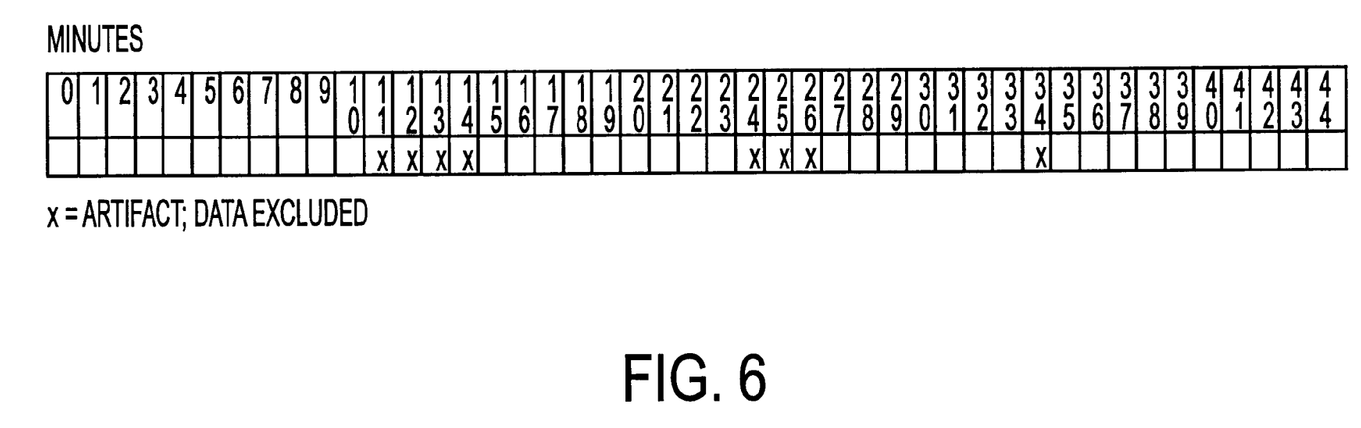
FIG. 6 is a chart showing identification of artifact and selection of minutes of an EGG recording for computer analysis.

In summary, after review of the raw EGG rhythm strip and respiration signal the minutes of EGG signal excluded from consideration and those selected for computer analysis for the above example are indicated in chart form in FIG. 6 and are as follows:
Preprandial Baseline minutes 0 through 10 selected
Ingestion of water, artifact; minutes 11 through 14 excluded
Postprandial minutes 15 through 23 selected
Artifact: minute 24 excluded
Artifact: minutes 25 and 26 excluded
Postprandial minutes 27 through 33 selected
Postprandial minutes 35 through 43 selected The data file created during the A/D conversion of the EGG signal 15 undergoes Fourier Transform (FT), an analysis of the frequencies contained in the EGG signal. The FTs are calculated and then recalculated as Running Spectral Analysis (RSA), a three dimensional plot. A calculation of the percentage of power in selected frequency bands are reports produced via the EGG analysis system 10. The EGG data is presented in four major frequency ranges which have been published and are followed by many clinical investigators; e.g., normal (2.5 to 3.75 cpm), bradygastria (1.0 to 2.5 cpm), tachygastria (3.75 to 10.0 cpm), and duodenal-respiratory (10.0 to 15.0 cpm). The data in these ranges are described in four ways: 1) the raw power (log $\mu V^2$); 2) the percentage distribution of the power in the specific ranges described above; and 3) the ratio of power based on postprandial to preprandial power; and finally, 4) the RSA of the EGG recording presented in a pseudo 3-D format.

Thus, once the RSA is developed based on the EGG signals, the RSA is analyzed and interpreted. Artifact appears in the RSA as broad-based, high power contours that clearly standout compared with the other peaks or as sawtooth type contours with many different peaks within the same time period. The minutes at which these artifactual peaks occur are compared with the minutes where artifact occurred in the raw EGG recording. The artifactual minute (s) in the raw data set are then deleted and the program is run again to obtain the new artifact free (or reduced artifact) RSA. The original digitized file of EGG data is saved intact. The new RSA is then re-examined and interpreted in a qualitative manner: normal, tachygastria, bradygastria, mixed tachyarrhythmia pattern before and after the water, load test. The interpretation is based on the frequencies where the peaks in the RSA are located, the raw analog EGG signal and the percentage distribution, as explained more fully below.

Figure 7:
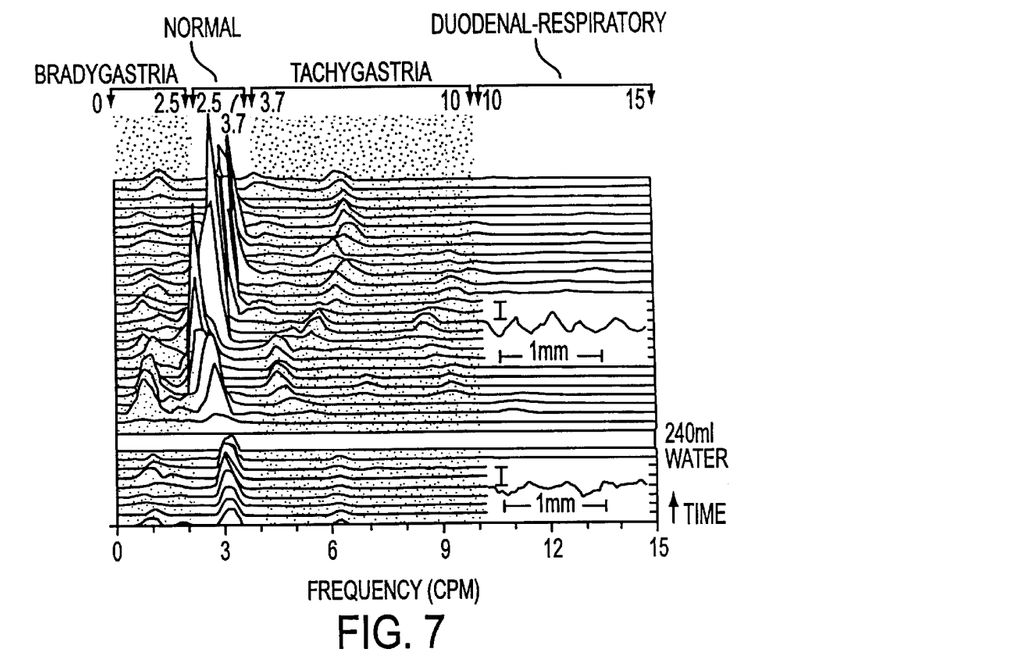
FIG. 7 shows a running spectral analysis (RSA) of a normal EGG recording before and after the subject drinks water.
Figure 8:
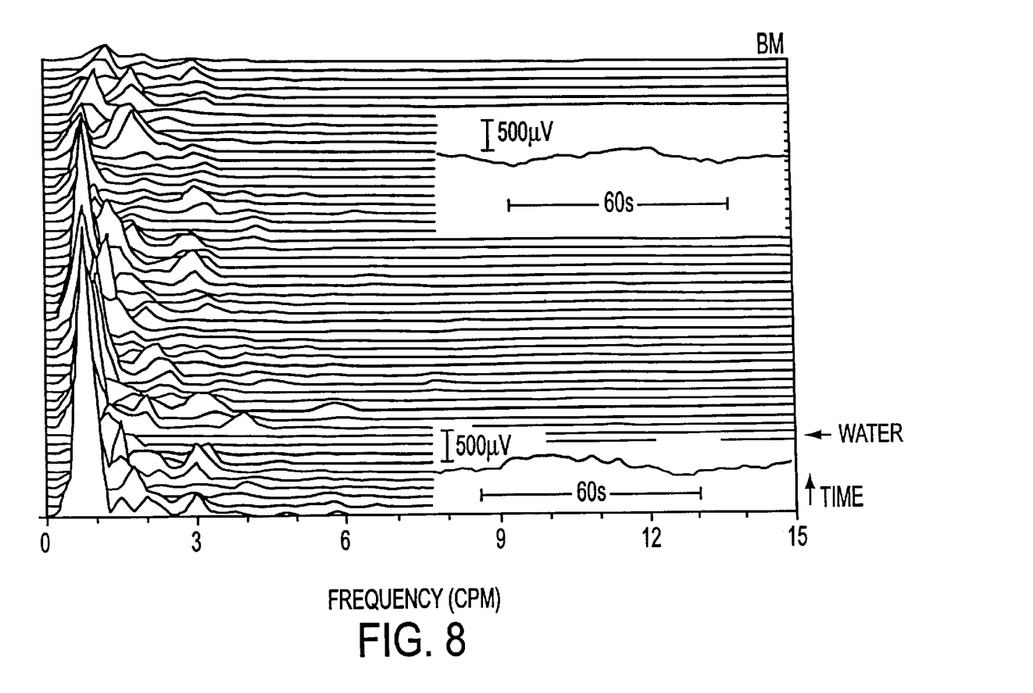
FIG. 8 shows a low amplitude Bradygastria RSA recorded from a patient with functional dyspepsia.
Figure 9:
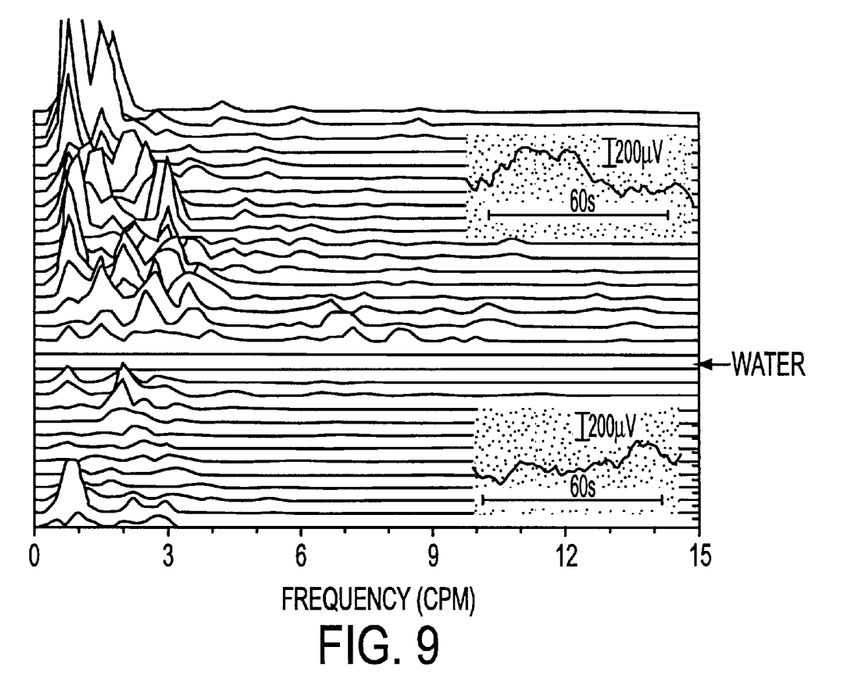
FIG. 9 shows a high amplitude Bradygastria RSA recorded from a patient with functional dyspepsia.
Figure 10:
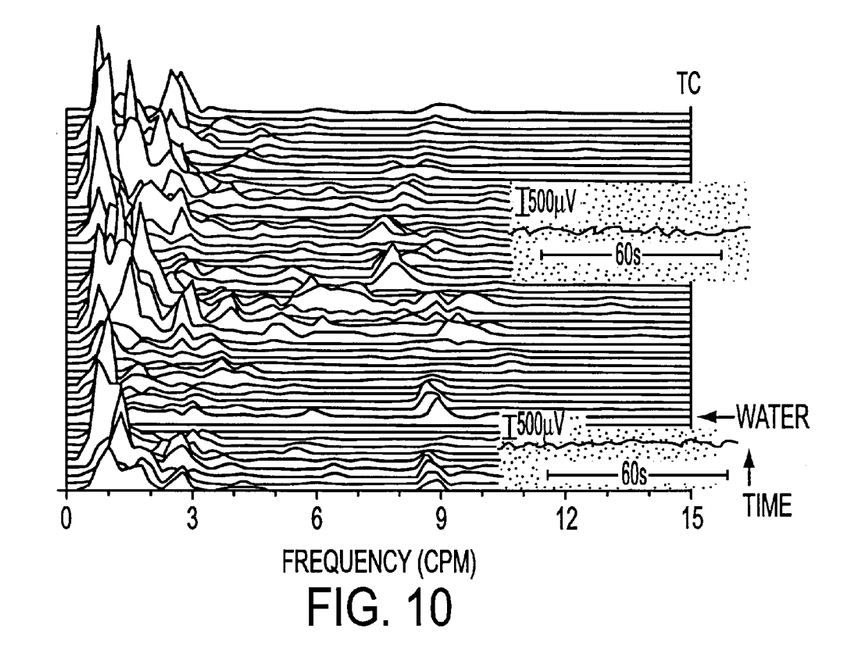
FIG. 10 shows a Tachgastria RSA from a patient with idiopathic gastroparesis.
Figure 11:
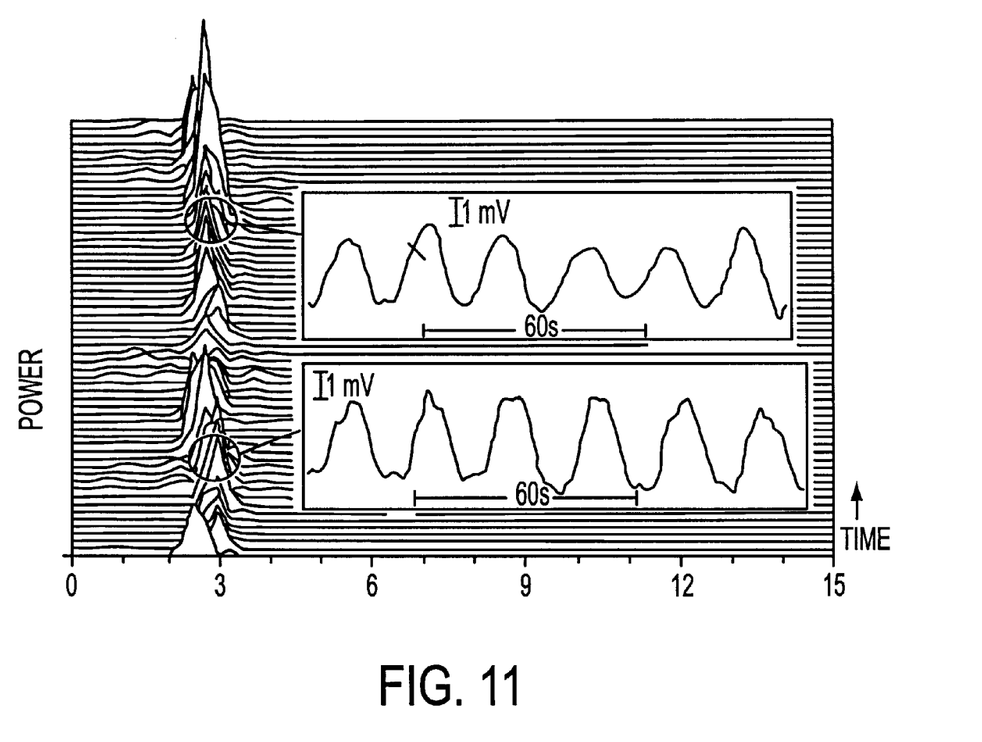
FIG. 11 shows an RSA from a patient with gastric outlet obstruction.

FIGS. 7–11 illustrate RSAs relating to gastric dysrhymias. FIG. 7 shows a running spectral analysis (RSA) of a normal EGG recording from a healthy patient before and after the patient drinks water. FIG. 8 shows a low amplitude Bradygastria RSA recorded from a patient with functional dyspepsia. FIG. 9 shows a high amplitude Bradygastria RSA recorded from a patient with functional dyspepsia. FIG. 10 shows a Tachygastria RSA from a patient with idiopathic gastroparesis. FIG. 11 shows an RSA from a patient with gastric outlet obstruction.

Next, a quantitative interpretation of the EGG signal 15 is performed using percentage distribution of EGG power across the frequencies from 1–15 cpm. The percentage distribution of power is calculated and then plotted on a graph. The graph has the normal range of EGG percentage a distribution (mean ±1 SD) before and 30 minutes after the water load test for the four ranges described above: normal, bradygastria, tachygastria and duodenal-respiratory frequencies. The volume of water ingested is also recorded. The individual patient's data is plotted against the ranges of normal subjects. Based on these plots, a diagnosis of normal EGG, tachygastria, bradygastria or mixed dysrhythmia is made.

The recording and interpretation of the clinical EGG requires a high-quality recording of the raw EGG signal and appropriate identification of artifact in the signal by use of the respiratory signal comparisons, an RSA with artifact removed, and analysis of the percentage distribution of EGG power in the relevant frequency ranges.

Thus, the system 10 performs three functions:
1) Produces a raw EGG signal that is interpretable because of the concomitant recording of the respiratory signal,
2) Produces an RSA that is interpretable because artifactual EGG signals are identified and excluded, and
3) Produces a percentage distribution for patients and control subjects for clinical interpretation of the EGG signal.

Although the method of detecting artifacts has been described with regard to detecting irregularities in the respiration signal 26 and corresponding EGG signal 15 as displayed on the strip chart recorder 16, it can be appreciated that since the respiration signal 26 and EGG signal 15 are sent to the A/D converter 18 and thus to the computer 20, artifact determination can be performed at the computer 20. For example, the computer software can receive the respiration signal 26 and the corresponding EGG signal 15 and, based a comparison of acceptable amplitudes and frequencies and the amplitudes and frequencies of the signals 15 and 26, artifacts may be determined. Further, the signals 15 and 26 (waveforms) may be displayed on a monitor of the computer and the artifacts can be flagged as they appear.

Figure 12:
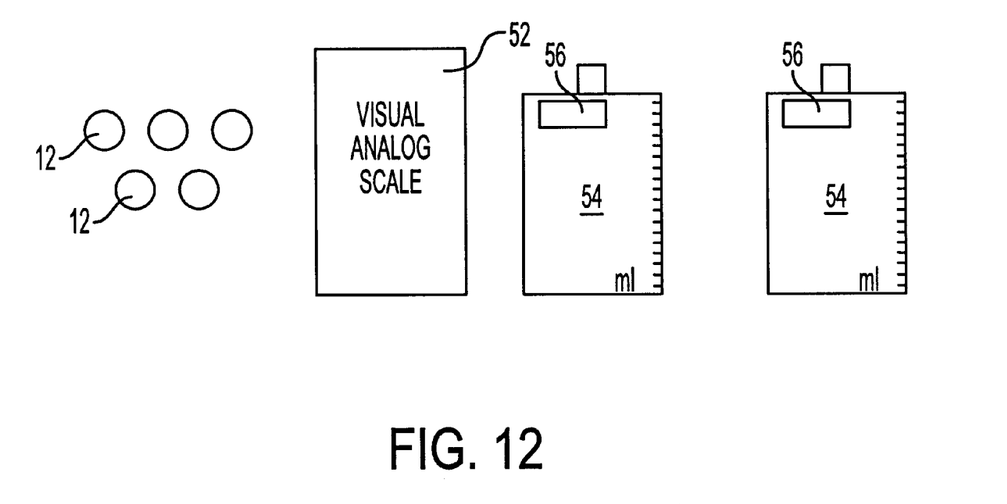
FIG. 12 shows a kit containing items for use in performing an EGG in accordance the invention.

With reference to FIG. 12, the present invention also provides a test kit, generally indicated at 50, for use in the EGG recording. The EGG test kit 50 contains the disposable components used to perform an EGG recording with the water load test. Using these components for each EGG test that is performed will contribute to the reliability and reproducibility of EGG recordings. The kit contains:

1) Five disposable, high quality electrodes 12,
2) A visual analog scale 52 for scoring the intensity of the selected symptoms before and after the water load is ingested, and
3) Two, one liter bottles 54 of spring water that are scored with ml marks every 20 ml for accurate measurement of the volume of water consumed during the water load test. A tear-off adhesive label 56 to record volume of water consumed is also attached to each bottle for placement on the patient's EGG recording or EGG report. The spring water also ensures a consistency of water source and taste for all EGG recordings. Various nutrients or other markers may be provided separately and added to the water to test specific gastric (intestinal or colonic) responses to carbohydrates, protein, fat or other materials.

While the invention has been described with reference to the exemplary embodiments thereof, those skilled in the art will be able to make various modifications to the described embodiments of the invention without departing from the true spirit and scope of the invention.

What is claimed is:

1. A system for processing signals indicative of detected myoelectrical activity, the system comprising:

electrodes to obtain first signals over time from a gastrointestinal organ in the abdominal cavity of a living being, the first signals including spurious signals as a result of artifact, a sensor to obtain second signals simultaneously as the first signals are obtained, the second signals being indicative of a respiratory function of the living being and include spurious signals indicative of artifact, and a processor containing software to analyze the first signals which occur at times when artifact is determined to not be present in both of the first and second signals.

2. The system according to claim 1, further including a recorder to receive and display simultaneously, the first and second signals including the spurious signals thereof.

3. The system according to claim 2, wherein said recorder is a strip chart recorder.

4. The system according to claim 1, wherein the processor is a computer.

5. The system according to claim 4, wherein the first signals are analog signals and the method including converting the analog signals to digital signals with the processor analyzing the digital signals.

6. The system according to claim 5, wherein an analog-to-digital converter converts the analog signals.

7. The system according to claim 1, wherein the second signals are analog signals and the method including converting the analog second signals to digital signals.

8. The system according to claim 1, wherein the sensor is part of a respiratory belt constructed and arranged to be fitted to a chest of the living being.

9. The system according to claim 1, wherein at least three electrodes are provided.

10. The system according to claim 1, further including amplifiers to amplify the first and second signals.

11. A method of identifying artifacts in signals indicative of detected myoelectrical activity, the method including:

providing electrodes to obtain first signals over time from a gastrointestinal organ in the abdominal cavity of a living being, the first signals including spurious signals as a result of artifact, providing a sensor to obtain second signals simultaneously as the first signals are obtained, the second signals being indicative of a respiratory function of the living being and include spurious signals indicative of artifact, recording the first and second signals simultaneously, identifying when artifacts occur by noting irregularities in both the recorded first and second signals during a particular time frame.

12. The method according to claim 11, wherein the step of obtaining the first signals includes obtaining myoelectric signals from the stomach.

13. The method according to claim 11, wherein the recording step includes recording the first and second signals on a strip chart recorder.

14. The method according to claim 11, wherein the sensor is provided in a respiration belt coupled to a chest of the living being.

15. A method of analyzing signals indicative of detected myoelectrical activity, the method including:

providing electrodes to obtain first analog signals over time from an internal organ of a living being, the first analog signals including spurious signals as a result of artifact, providing a sensor to obtain second analog signals simultaneously as the first analog signals are obtained, the second analog signals being indicative of a respiratory function of the living being and include spurious signals indicative of artifact, recording the first and second analog signals simultaneously, identifying when artifacts occur by noting irregularities in both the recorded first and second analog signals during a particular time frame, converting the first analog signals to digital signals, and analyzing the digital signals which occur at times when artifact is not present, wherein the digital signals are analyzed by software wherein only digital signals which occur when no artifacts are present are analyzed.

16. The method according to claim 15, wherein the step of obtaining the first signals includes obtaining signals of the stomach.

17. The method according to claim 15, wherein the recording step includes recording the first and second signals on a strip chart recorder.

18. The method according to claim 15, wherein the sensor is provided in a respiration belt coupled to a chest of the living being.

19. A method of monitoring myoelectrical activity of the stomach of a person comprising:

mounting electrodes on the abdomen of the person to obtain first analog signals from the stomach over time, the first analog signals including spurious signals as a result of artifact, mounting a sensor to the person to obtain a plurality of second analog signals simultaneously as the first analog signals are obtained, the second analog signals being indicative of a respiratory function of the person and include spurious signals indicative of artifact, consuming, by the person, water in a specific time frame until the stomach is substantially full to stimulate gastric electro-contractile activity while recording the first and second analog signals simultaneously, continuing to record the first and second analog signals simultaneously for a period of time after consumption of water, identifying, during the recording of the first and second signals, the occurrence of artifacts by noting irregularities in both the first and second analog signals during a particular time frame, converting the first analog signals to digital signals, and analyzing the digital signals which occur at times when artifact is not present.

20. The method according to claim 19, wherein the time frame is about five minutes.

21. The method according to claim 19, wherein the first and second signals are recorded on a chart of a strip chart recorder, the method includes marking the start and finish time of the water consumption and the amount of water consumed on the chart.

22. A kit for use in recording myoelectric activity of the stomach of a person, the kit comprising:
- a plurality of disposable electrodes,
- a visual analog scale for scoring an intensity of selected symptoms at various times, and
- two, one liter bottles of spring water, each bottle being scored with ml marks for accurate measurement of the volume of water consumed from the bottle.

23. The kit according to claim 22, wherein five electrodes are provided.

24. The kit according to claim 22, wherein each bottle includes a tear-off adhesive label to record volume of water consumed from the bottle.

25. The system of claim 1, wherein the gastrointestinal organ is the stomach.

26. The system of claim 1, wherein the gastrointestinal organ is the duodenum.

27. The system of claim 1, wherein the gastrointestinal organ is the small intestine.

28. The system of claim 1, wherein the gastrointestinal organ is the colon.

29. The method according to claim 11, wherein the step of obtaining the first signals includes obtaining myoelectric signals from the duodenum.

30. The method according to claim 11, wherein the step of obtaining the first signals includes obtaining myoelectric signals from the small intestine.

31. The method according to claim 11, wherein the step of obtaining the first signals includes obtaining myoelectric signals from the colon.

* * * * *